United States Patent [19]

Eriksson et al.

[11] Patent Number: 4,583,573

[45] Date of Patent: Apr. 22, 1986

[54] COLLECTION APPARATUS

[75] Inventors: Rolf B. Eriksson, Solna; Bertil Jansson, Spånga; Jörgen Sjödahl, Knivsta, all of Sweden

[73] Assignee: LKB-Produkter AB, Bromma, Sweden

[21] Appl. No.: 659,967

[22] Filed: Oct. 11, 1984

[30] Foreign Application Priority Data

Oct. 18, 1983 [SE] Sweden .............................. 8305707

[51] Int. Cl.⁴ ................................................ B65B 3/34
[52] U.S. Cl. ...................................... 141/250; 141/153
[58] Field of Search .................. 141/1, 128, 129, 130, 141/153, 250

[56] References Cited

U.S. PATENT DOCUMENTS

| | | | |
|---|---|---|---|
| 2,672,271 | 3/1954 | Gorham | 141/153 X |
| 2,880,764 | 4/1959 | Pelavin | 141/130 |
| 3,004,567 | 10/1961 | Snow et al. | 141/153 X |
| 3,124,172 | 3/1964 | Paxson, Jr. | 141/130 |
| 4,166,483 | 9/1979 | Nordlund | 141/1 |

Primary Examiner—Stephen Marcus
Assistant Examiner—Mark Thronson
Attorney, Agent, or Firm—Fisher, Christen & Sabol

[57] ABSTRACT

A method of using a collection apparatus as well as the collection apparatus itself. The latter includes collection receptacles, a drip nozzle, and a component for bringing about a relative movement between the receptacles and the drip nozzle at predetermined times to collect the drops emitted by the drip nozzle, in the different receptacles. The time between the drops is measured by a time measurement circuit. The lower and the upper time limits for a time interval within which the next drop is expected, are calculated by a time limit calculating circuit. A blocking circuit is adapted to compare the time measured after the latest drop with the calculated time limits, and to block the relative movement when the measured time lies between these time limits. The blocking circuit is adapted to permit the relative movement when the expected drop has been emitted within the time limits.

2 Claims, 1 Drawing Figure

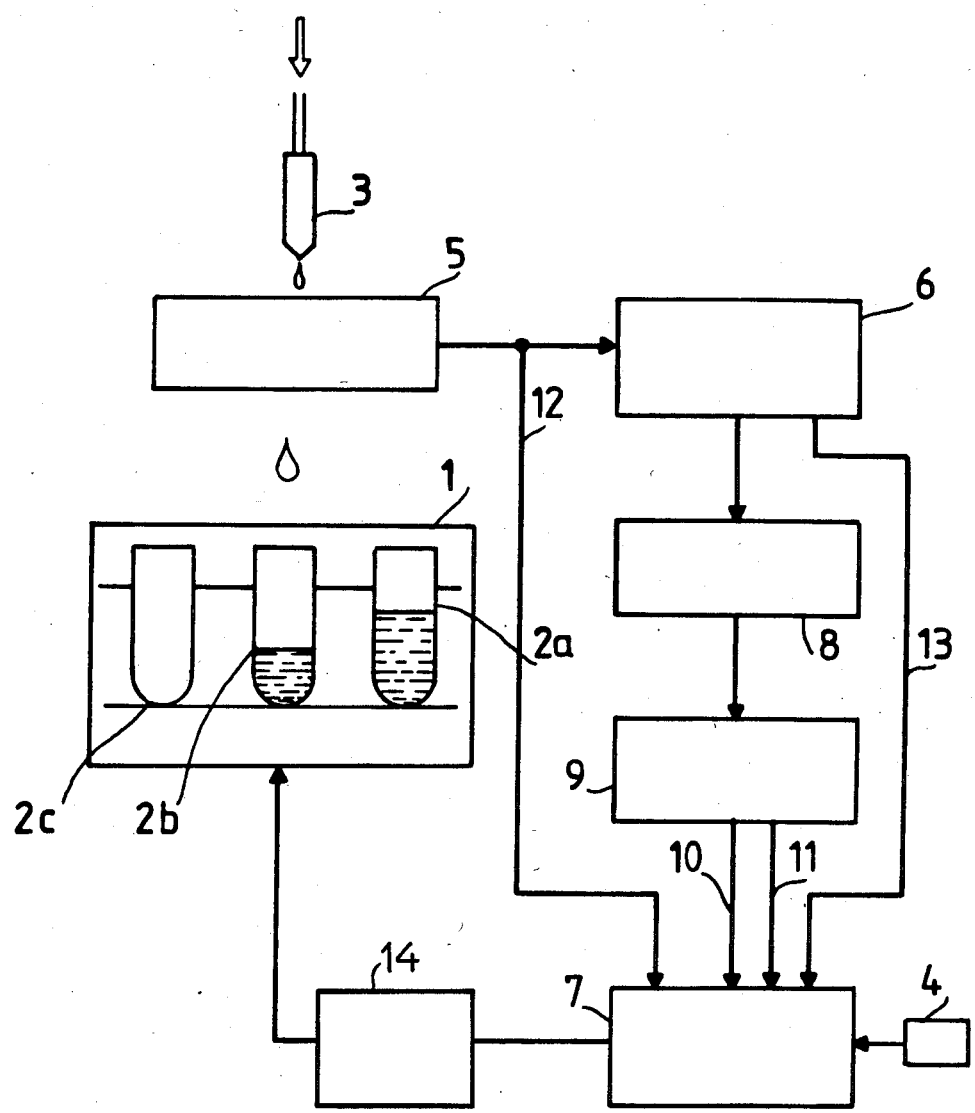
FIGURE

COLLECTION APPARATUS

TECHNICAL FIELD

The present invention relates to a method using a collection apparatus comprising collection receptacles, a drip nozzle, and means for bringing about a relative movement between the receptacles and the drip nozzle at predetermined times to collect the drops emitted by the drip nozzle, in the different receptacles as well as the collection apparatus for carrying the method into effect.

BACKGROUND ART

In known collection apparatuses of the fraction collection type there is no synchronization of the switching of the receptacles, i.e. test tubes, with the emission of drops from the drip nozzle when collection is carried out by means of time-programmed switching. This leads to drops that appear in connection with a tube switching, occurring between the tubes which is disadvantageous, since, hereby, sample fluid is lost and at the same time the fraction collector is dirtied. Radioactive overflow would, moreover, be obtained in case the sample fluid would be radioactive.

DISCLOSURE OF INVENTION

The object of the present invention is to bring about a collection apparatus of the above mentioned type, in which switching of the receptacles cannot take place when a drop is falling from the drip nozzle.

This is attained by the method and the collection apparatus according to the invention.

The invention involves a method using a collection apparatus, which comprises collection receptacles, a drip nozzle, and means for bringing about a relative movement between the receptacles and the drip nozzle at predetermined times to collect the drops emitted by the drip nozzle, in the different receptacles. The method includes measuring the time between the drops, calculating the lower and the upper time limits for an interval within which the next drop is expected, comparing the time measured after the latest drop with the calculated time limits, and blocking said relative movement as long as the measured time is between the time limits. In one embodiment the relative movement is released when the expected drop has been emitted within the calculated time limits as well as when the measured time has exceeded the upper time limit.

The invention also involves collection apparatus which includes collection receptacles, a drip nozzle, and means for bringing about a relative movement between the receptacles and the drip nozzle at predetermined times to collect the drops emitted by the drip nozzle, in the different receptacles. There is a time measurement circuit for measuring the time between the drops. There is also a time limit calculating circuit for calculating the lower and the upper time limits of an interval within which the next drop is expected. A blocking circuit is used to compare the time measured after the last drop with the calculated time limits, and to block said relative movement when the measured time is between the time limits. In one embodiment, the blocking circuit is adapted to release the relative movement when the expected drop has been emitted within the calculated time intervals as well as when the measured time has exceeded the upper time limit.

BRIEF DESCRIPTION OF DRAWING

The invention will be described more in detail below with reference to the attached drawing on which the single FIGURE shows an embodiment of a collection apparatus according to the invention.

PREFERRED EMBODIMENT

The drawing shows an embodiment of a collection apparatus according to the invention. The collection apparatus shown can be e.g. a fraction collector comprising a schematically shown rack 1 for receptacles of which merely three denoted 2a, 2b and 2c, respectively, are shown. The collection apparatus shown is supposed to be of the type where the rack 1 is moveable relative to a drip nozzle 3 from which drops of a liquid are emitted to be collected in the different receptacles 2a, 2b and 2c. Instead of using a moveable rack 1 it is of course possible to use a moveable drip nozzle 3.

The shown rack 1 is supposed to be mechanically driven by means of driving means, not shown, to bring the receptacles under the drip nozzle 3 in sequence. The driving means, not shown, is supposed to obtain driving orders from a driving order transmitter 4 which, in the embodiment shown, is supposed to be adapted to transmit its driving orders at predetermined times.

In order to prevent that the drops emitted by the drip nozzle end up between the receptacles on the rack 1 in connection with a receptacle switch there is, in the embodiment shown, a drop detector 5, e.g. a combination of a light emitting diode and a phototransistor, which is adapted to detect drops emitted by the drip nozzle 3 and in connection herewith to supply a signal to a time measurement circuit 6. This time measurement circuit 6 is adapted to measure the time between the drops, store the measured time intervals between a predetermined number of drops, and via a wire 13 transfer the information about the time that has elapsed since the latest drop was detected, to a blocking circuit 7 which will be described more in detail below.

The information about the time intervals between the drops is in the embodiment shown, transferred from the time measurement circuit 6 to a mean value calculating circuit 8 which is adapted to calculate the mean value of the time intervals between the drops from the drip nozzle 3 on the basis of a predetermined number of the measured time intervals.

The mean value calculating circuit 8 is connected to a time limit calculating circuit 9, which is adapted to calculate the lower and the upper time limits of a time interval within which it is expected that the next drop is emitted from the drip nozzle 3. The time limits can e.g. be ±25% of the mean value calculated by the mean value calculating circuit 8. A signal corresponding to the lower time limit is supplied to the blocking circuit 7 via a wire 10, while a signal corresponding to the upper time limit is supplied to the blocking circuit 7 via a wire 11.

The blocking circuit 7 is connected between the driving order transmitter 4 and the driving means, 14 for driving the rack 1 with the receptacles 2a, 2b and 2c. According to the invention with the blocking circuit 7 is adapted to compare the time measured after the latest drop, that is supplied from the time measurement circuit 6 via the wire 13 with the lower and the upper time limits that are supplied from the time limit calculating circuit 9 via the wires 10 and 11. When the time after the latest emitted drop, measured by means of the time measurement circuit, lies between the calculated time limits, the blocking circuit 7 blocks the driving of the rack 1, since the next drop from the drip nozzle 3 is expected to appear between these time limits. As soon as the drop has appeared a signal is transmitted from the drop detector 5 to the blocking circuit 7 via a wire 12, which signal unblocks the blocking circuit and permits driving of the rack 1 to bring a new receptacle under the drip nozzle 3.

If the time interval after the latest drop exceeds the upper limit calculated by the time limit calculating circuit 9, i.e. there is no drop appearing within the calculated time interval, the blocking circuit will transfer the driving order from the driving order transmitter 4 to the driving means for driving the rack 1.

Thus, in the collection apparatus according to the invention no drops will end up between the receptacles provided of course that the drops appear according to a statistically predictable pattern.

We claim:

1. Collection apparatus comprising collection receptacles, a drip nozzle from which drops can be emitted, means for bringing about a relative movement between the receptacles and the drip nozzle at predetermined times to collect the drops emitted by the drip nozzle, in the different receptacles, a time measurement circuit for measuring the time between the drops, a time limit calculating circuit for calculating the lower and the upper time limits of an interval within which the next drop is expected, and a time-measuring blocking circuit to compare the time measured after said next drop has been emitted by the nozzle with the calculated time limits, and to block said relative movement when the measured time is between the time limits.

2. Apparatus according to claim 1 wherein the blocking circuit is adapted to release said relative movement when the expected drop has been emitted within the time limits as well as when the measured time has exceeded the upper time limit.

* * * * *